United States Patent [19]

Cornforth et al.

[11] 4,073,815
[45] Feb. 14, 1978

[54] PROCESS FOR THE PREPARATION OF 2,2-BIS(3,5-DI-T-BUTYL-4-HYDROXY-PHENYL)PROPANE

[75] Inventors: John W. Cornforth, Lewes; John A. Schofield, Sittingbourne; Sidney J. French, Canterbury, all of England; Robin T. Gray, Heemstede, Netherlands

[73] Assignee: Shell Oil Company, Houston, Tex.

[21] Appl. No.: 733,816

[22] Filed: Oct. 19, 1976

[30] Foreign Application Priority Data

Oct. 21, 1975 United Kingdom ............... 43140/75

[51] Int. Cl.$^2$ .................. C07C 37/00; C07C 39/16

[52] U.S. Cl. ................................................ 260/619 A
[58] Field of Search .................................... 260/619 A

[56] References Cited

U.S. PATENT DOCUMENTS

| 3,116,336 | 12/1963 | Van Winkle | 260/6.9 A |
| 3,207,794 | 9/1965 | Harnes et al. | 260/6.9 A |
| 3,221,060 | 11/1965 | Abbert et al. | 260/6.9 A |

*Primary Examiner*—Norman Morgenstern

[57] ABSTRACT

A process for the preparation of 2,2-bis(3,5-di-t-butyl-4-hydroxyphenyl)propane by reacting isobutylene with diphenylolpropane in the presence of a substantially anhydrous aromatic sulfonic acid.

6 Claims, No Drawings

PROCESS FOR THE PREPARATION OF 2,2-BIS(3,5-DI-T-BUTYL-4-HYDROXYPHENYL)-PROPANE

BACKGROUND OF THE INVENTION

The invention is concerned with a process for preparing 2,2-bis (3,5-di-t-butyl-4-hydroxyphenyl)propane by reacting isobutylene with diphenylolpropane and with 2,2-bis(3,5-di-t-butyl-4-hydroxyphenyl)propane so formed.

It is known from U.K. Pat. specification No. 781,768 to alkylate bisphenylol alkanes in the presence of solvents and Friedel-Craft catalysts such as sulfuric acid, p-toluene sulfonic acid, boron trifluoride and acid-activated clays. As can be seen from the examples of the said U.K. specification this process results in a poor yield of the desired tetraalkylated bisphenylol alkane which is also difficult to isolate. The reason for this is that, unlike the alkylation of monophenols e.g. phenol itself, a competitive reaction accompanies the alkylation of bisphenol alkanes. This competitive reaction is the cleavage of the bisphenolic skeleton to form phenol and alkyl phenol followed by the disproportionation, polymerization and alkylation thereof. This competitive reaction is particularly a problem when it is desired to produce mainly the tetra-alkylated derivatives.

It has now been discovered that, by carrying out the reaction between isobutylene and diphenylolpropane in the presence of a substantially anhydrous aromatic sulfonic acid a reaction product containing improved yields of desired tetra-alkylated product is obtained from which the desired product may easily be extracted.

2,2-bis(3,5-di-t-butyl-4-hydroxyphenyl)propane is used for a variety of purposes such as for the stabilization of natural or synthetic rubbers and plastics.

SUMMARY OF THE INVENTION

A process for producing 2,2-bis(3,5-di-t-butyl-4-hydroxyphenyl)propane at improved yields comprises reacting diphenylolpropane and excess isobutylene in the presence of a substantially anhydrous aromatic sulfonic acid in a hydrocarbon solvent at a temperature between about 30° and about 70° C. The process is advantageously carried out at two temperature levels, first between about 30° and about 55° C until substantially all of the product is di- or trialkylated, then at about 55° C to about 70° C. When the anhydrous aromatic sulfonic acid is soluble in the solvent, the catalyst can be added in portions between about 15 and about 40% of the total to be used, where the total catalyst used is between about one-half to about one-tenth of the moles of diphenylolpropane initial present.

DESCRIPTION OF THE PREFERRED EMBODIMENTS

Accordingly, the present invention is concerned with a process for the preparation of 2,2-bis(3,5-di-t-butyl-4-hydroxyphenyl)propane which comprises reacting diphenylolpropane with isobutylene in the presence of an organic solvent and a substantially anhydrous aromatic sulfonic acid. The reaction is preferably carried out under an atmosphere of isobutylene at a pressure of between about 800 and about 1400 mm Hg abs., a pressure of from about 900 to about 1300 mm Hg abs being particularly preferred.

Any aromatic sulfonic acid which does not contain another group attached thereto which will interfere may be used in this invention. (By aromatic sulfonic is meant, a compound having a sulfonic acid group attached through the sulfur atom to the aromatic carbon of the aromatic ring). Preferred aromatic sulfonic acids include para-bromobenzene sulfonic acid benzene sulfonic acid and para-toluene sulfonic acid, the latter two being particularly preferred. The most preferred aromatic sulfonic acid is paratoluene sulfonic acid.

The amount of diphenylolpropane used is suitably from about 150 to about 450 g/liter of solvent, preferably from about 200 to about 400 g/liter.

Suitable organic solvents for the process may be any organic solvent which does not react with either the reactants or the products and in which the reactants are at least partially soluble at the reaction temperature. Preferably, hydrocarbon solvents, such as benzene, toluene or cyclohexane, are used.

The reaction is carried out at a temperature in the range of from about 30° C to about 70° C. If a single temperature is to be used the preferred range is between about 30° C and about 55° C. The preferred method of carrying out the reaction is to run it at two temperature levels, a lower temperature level until greater than about 70, preferably greater than about 80% of the diphenylolpropane has been converted to the di- and/or tri-alkylated product and a higher temperature level for the final alkylation. The preferred lower temperature level is between about 30° C and about 55° C, most preferably between about 40° C and about 50° C. The preferred higher temperature level is between about 55° C and about 70° C, most preferably between about 60° C and about 70° C. The formation of di- and trialkylated products may be detected by following the course of the reaction by gas/liquid chromatography (GLC). In most of the solvents suitable for the reaction, the formation of the di- and trialkylated products has been found to coincide with the complete solubilization of diphenylol propane. (A preferred column for determining the ratio of products in the GLC is 5ft 3% SE-30 column, temperature program 150°-200° C at 10°/min.)

The amount of substantially anhydrous aromatic acid used as catalyst may vary between wide limits. Advantageously the amount is such that the molar ratio of diphenylolpropane to catalyst is between about 2:1 and about 10:1, preferably between about 3:1 and about 9:1.

It is advantageous not to have the whole amount of catalyst in solution at the beginning of the reaction, i.e. it is advantageous to gradually increase the amount of dissolved catalyst during the reaction until an amount in the aforesaid range is present. This may be achieved in several ways. Firstly, if the solvent employed rapidly dissolves the desired total amount of catalyst at the reaction temperature, e.g. when benzene or toluene is used as solvent, then the catalyst may be added in several portions to the reaction mixture as the reaction proceeds. A preferred method of carrying out the reaction is to add about 115 to about 40 weight percent of the desired amount of catalyst initially then about 15 to about 40 weight percent of the desired amount of catalyst at intervals of greater than about 1 hr, preferably between about 1 hr to about 5 hrs, most preferably 1 hour to about 3 hrs. Secondly, also if the solvent rapidly dissolves the desired total amount of catalyst at the reaction temperature, then the desired total amount of catalyst may be absorbed on a suitable carrier from which it is slowly released into the solvent. Suitable supports include diatomaceous silica supports. Thirdly, if the solvent only slowly dissolves the desired total amount of catalyst at the reaction temperature, e.g. when cyclohexane is used as solvent, then the desired total amount of catalyst may initially be present in the reaction mixture.

Suitable reaction times range from about 4 to about 50 hrs, preferably from about 5 to about 45 hrs.

The substantially anhydrous aromatic sulfonic acid may be prepared from the aromatic sulfonic acid monohydrate by refluxing it in solvents such as benzene, toluene or cyclohexane, the water being removed as the corresponding azeotrope. In the case of solvents which rapidly and completely dissolve the catalyst it is necessary to remove at least part of or all of the solvent. In the case of solvents which don't rapidly dissolve the catalyst, the mixture resulting from the refluxing operation may be used as such in the process. The substantially anhydrous aromatic sulfonic acids may also be prepared by heating the corresponding monohydrate under vacuum. (By substantially anhydrous it is meant that there is less than 5, particularly less than 1, and preferably less than 0.1 and most preferably less than about 0.01 weight percent water present in the catalyst.)

The products prepared by the process according to the present invention may be worked up by conventional techniques. Suitably the crude product is washed and the solvent evaporated (or partially evaporated) to produce a crystalline product. This crystalline product may be purified by crystallization from conventional solvents.

The process of this invention shows yields by GLC of greater than about 70%, preferably greater than 80% and most preferably greater than 90% based on the diphenylolpropane.

The following Illustrative Embodiments are presented for illustrative purposes only and should not be taken to limit the scope of the invention.

ILLUSTRATIVE EMBODIMENT I 7.5 g of powdered predried p-toluene sulfonic acid (TSA), prepared by refluxing the monohydrate with toluene, removing the water as the toluene-water azeotrope and crystallizing the anhydrous catalyst from the solution, was added to a stirred suspension of 228.0 g of finely divided diphenylolpropane (DPP) in benzene (AR, 1 liter). The reaction was stirred in an oil bath at 51° C under a pressure of isobutylene (1080 mm; ex British Oxygen Company; 99% purity) until solution was complete (2 hours). Further portions of acid (7.5 g, 7.5 g and 4.0 g) were made at 2, 5 and 23 hours respectively, and the reaction conditions maintained for 30 hours total. At this time, analysis of a sample by GLC indicated a mixture comprising about 80% of 2,2-bis(3,5-di-t-butyl-4-hydroxyphenyl)propane and about 12% cleavage products.

The clear solution was then washed with water (3 × 100ml), saturated sodium bicarbonate solution (1 × 100 ml) and water (1 × 100 ml). The organic phase was dried ($M_gSO_4$) and evaporated under reduced pressure (water bath temperature 60° C). The crude crystalline product was recrystallized from petroleum ether (60° to 80° C fraction, 1400 ml) firstly at ambient temperature then at −10° C, giving 315.5 g (70%) of 2,2-bis(3,5-di-t-butyl-4-hydroxyphenyl)propane as colorless plates m.p. 153° C to 155.5° C. A second recrystallization from the same solvent gave 280.0 g (62%) of colorless plates m.p. 155° to 157.5° C.

Table 1

| Illustrative Embodiments | Concentration of DPP in benzene (g/100 ml) | Moles DPP | Mole Ratio DPP/TSA | Catalyst |
| --- | --- | --- | --- | --- |
| I | 22.8 | 0.02 | 4/1 | TSA on[4] Celite 545 |
| II | " | 0.06 | 4/1 | TSA on Celite 545 |
| III | " | 0.06 | 4/1 | TSA |
| IV | " | 0.2 | 8/1 | " |
| V | " | 0.5 | 8/1 | " |
| VI | " | 1.0 | 8/1 | " |

| Oil bath Temp (° C) | Isobutylene pressure mm | Reaction Time (Hr) | % product[2] by GLC | % product[3] isolated |
| --- | --- | --- | --- | --- |
| 47 | 1020 | 42 | 95 | 60 |
| 49 | 1060 | 20 | 79 | 53 |
| 49 | 1060 | 10 | 87 | 62 |
| 47 | 1080 | 18 | 80 | 64 |
| 47–55 | 1080 | 43 | 90 | 71 |
| 52 | 1080 | 23 | 74 | 67 |

[1]in each case the acid was predried.
[2]2,2-bis (3,5-di-t-butyl-4-hydroxyphenyl)propane.
[3]only the 1st crop of the first recrystallization reported.
[4]diatomaceous silica.

ILLUSTRATIVE EMBODIMENT II

Six further experiments were carried out under the conditions described in Table I. The catalyst used in Illustrative Embodiments I and II using the total amount of TSA absorbed on Celite 545 comprised 0.01 mole of acid/4 g of support.

ILLUSTRATIVE EMBODIMENT III p-Toluene sulfonic acid monohydrate (7.7 g; 0.041 mole) was suspended in cyclohexane (225 ml) and the vigorously stirred mixture was heated under reflux using a Dean and Stark trap until no further water was removed. The mixture was cooled to an internal temperature of 36° C, diphenylolpropane (57 g; 0.25 mole) added and the mixture stirred vigorously under an atmosphere of isobutylene (constant pressure head of 30 cm) for a period of 180 minutes. The internal temperature of the reaction mixture was maintained at 42°–45° C throughout this period. The temperature was then raised to 65° C over a period of 15 minutes and finally maintained at this temperature for a further 120 minutes.

The pressure was then released, water (25 ml) was added and the hot mixture stirred vigorously for 10 minutes. The aqueous layer was then removed and the hot cyclohexane solution washed with a further portion (25 ml) of water and finally with saturated sodium bicarbonate solution (10 ml). The hot cyclohexane solution was decanted, concentrated by distillation to a total weight of about 200 g and then cooled at 4° C. The mixture was filtered, the precipitate washed with cyclohexane (50 ml) cooled to about 7° C and then dried in a vacuum oven to give 2,2-bis(3,5-di-t-butyl-4-hydroxyphenyl)propane (81.4 g; 71.5%) m.p. 151°–155° C.

A sample was recrystallized from n-heptane to give material m.p. 153–155.5° C.

ILLUSTRATIVE EMBODIMENT IV p-Toluene sulfonic acid monohydrate (7.7 g; 0.041 mole) was suspended in n-heptane (225 ml) and the vigorously stirred mixture was heated under reflux using a Dean and Stark trap until no further water was removed. The mixture was cooled to 45° C, diphenylolpropane (57 g; 0.25 mole) added and the mixture stirred vigorously under an atmosphere of isobutylene (constant pressure head of 30 cm). The temperature of the reaction mixture was maintained at 45° C for 2 hours and then at 60° C for a further 1 hour.

The pressure was then released, water (25 ml) was added and the hot mixture stirred vigorously for 10 minutes. The aqueous layer was then removed and the hot n-heptane solution washed with a further portion (25 ml) of water and finally with saturated sodium bicarbonate solution (10 ml). The hot n-heptane solution was decanted, concentrated by distillation to a total weight of about 180 g and then cooled at about 15° C. The product was isolated by filtration and dried in a vacuum oven to give 2,2-bis(3,5-di-t-butyl-4-hydroxyphenyl)propane (56 g; 50%), m.p. 120°–150° C.

ILLUSTRATIVE EMBODIMENT V

Benzene sulfonic acid (7.1 g; 0.045 mole) was dried by azeotroping with cyclohexane (225 ml). The mixture was cooled to 45° C, diphenylolpropane (57 g; 0.25 mole) added and the mixture stirred vigorously under an atmosphere of isobutylene (constant pressure head of 30 cm). The temperature of the reaction mixture was maintained at 45° C for 1 hour, then raised to 65° C over a period of 15 minutes and maintained at this temperature for a further 1 ¾ hours.

The reaction mixture was washed in the same was as in Illustrative Embodiment IV concentrated by distillation to a total weight of about 207 g and then cooled at 4° C. The product was isolated by filtration, washed with cold cyclohexane (25 ml) and dried in a vacuum oven to give 2,2-bis(3,5-di-t-butyl-4-hydroxyphenyl)propane (69.5 g; 58%), m.p. 148°–153.5° C.

ILLUSTRATIVE EMBODIMENT VI p-Toluene sulfonic acid monohydrate (7.7 g 0.041 mole) was dehydrated with cyclohexane (225 ml), the reaction mixture cooled to 45° C and diphenylolpropane (57 g; 0.25 mole) added with vigorous stirring. The apparatus was fitted with an overhead condenser cooled by a mixture of solid $CO_2$ and propan-2-ol and isobutylene was passed into the reaction mixture (below the surface of the reaction mixture). After a period of 2 hours, during which the temperature of the reaction mixture had fluctuated between 35° C and 50° C, the temperature was raised to 65° C and maintained at this level for a further 3 hours. The reaction mixture was worked up in the same way as in Illustrative Embodiment IV to give 2,2-bis(3,5-di-t-butyl-4-hydroxyphenyl)propane (59.5 g; 52.5%), m.p. 142°–149° C.

ILLUSTRATIVE EMBODIMENT VII p-Toluene sulfonic acid monohydrate (7.7 g; 0.041 mole) was dehydrated with cyclohexane (225 ml), the reaction mixture cooled to 45° C and diphenylolpropane (57 g; 0.25 mole) added with vigorous stirring. The apparatus was fitted with an overhead condenser cooled by a mixture of solid $CO_2$ and propan-2-ol and isobutylene was passed into the reaction mixture (below the surface of the reaction mixture). The rate of flow was adjusted so as to give the minimum reflux from the condenser and hence minimum cooling of the reaction mixture. After a period of 2 hours, during which the temperature of the reaction mixture had fluctuated between 33° C and 45° C, the temperature was slowly raised to 65° C over a period of 20 minutes and maintained at this level for a further 160 minutes. The reaction mixture was worked up in the same way as in Illustrative Embodiment IV to give 2,2-bis(3,5-di-t-butyl-4-hydroxyphenyl)propane (67 g; 59.5%), m.p. 149°–154.5° C.

ILLUSTRATIVE EMBODIMENT VIII

For comparative purposes, Illustrative Embodiment I was repeated using para-toluene sulfonic acid monohydrate.

Analysis of a sample of the product by GLC indicated a mixture comprising less than 50% of 2,2-bis(3,5-di-t-butyl-4-hydroxyphenyl)propane.

We claim as our invention:

1. A process for producing 2,2-bis(3,5-di-t-butyl-4-hydroxyphenyl)propane which comprises contacting diphenylolpropane and isobutylene in a hydrocarbon solvent at a temperature between about 30° and about 70° C in the presence of a substantially anhydrous p-toluene sulfonic acid catalyst.

2. The process of claim 1 wherein the diphenylolpropane is at an initial concentration of about 150 g to about 450 g/liter of solvent and the isobutylene is present at a pressure of between about 800 and about 1400 mm Hg abs.

3. The process of claim 2 where the molar ratio of diphenylolpropane to total catalyst is between about 2:1 and about 10:1.

4. The process of claim 3 where the solvent is selected from the group consisting of benzene, toluene, cyclohexane and mixtures thereof.

5. The process of claim 3 where the temperature is held at a level of between about 30° and about 55° C until greater than about 70% of the diphenylolpropane is converted to a di- and/or trialkylated product then raise and hold the temperature at a level between about 55° and about 70° C.

6. The process of claim 5 where the solvent is selected from the group consisting of benzene, toluene and mixtures thereof, the catalyst is initially present at a level in the range of about 15% about 40% of the total to be added and subsequent portions of about 15% to about 40% of the total catalyst are added at intervals of greater than about 1 hr.

* * * * *